US009637546B2

(12) United States Patent
Olive et al.

(10) Patent No.: US 9,637,546 B2
(45) Date of Patent: *May 2, 2017

(54) PD-1 ANTIBODIES AND PD-L1 ANTIBODIES AND USES THEREOF

(71) Applicants: Universite d'Aix Marseille, Marseilles (FR); INSERM (Institut National de la Sante et de la Recherche Medicale), Paris (FR); Institut Paoli Calmettes, Marseilles (FR)

(72) Inventors: Daniel Olive, Marseilles (FR); Nacer-Eddine Serriari, Amiens (FR); Jacques Nunes, Marseilles (FR); Marguerite Ghiotto, Marseilles (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/282,319

(22) Filed: May 20, 2014

(65) Prior Publication Data

US 2014/0335093 A1 Nov. 13, 2014

Related U.S. Application Data

(62) Division of application No. 13/148,420, filed as application No. PCT/EP2010/051563 on Feb. 9, 2010, now Pat. No. 8,741,295.

(30) Foreign Application Priority Data

Feb. 9, 2010 (EP) .................................. 09305119

(51) Int. Cl.
| | | |
|---|---|---|
| *A61K 39/395* | (2006.01) | |
| *C07K 16/00* | (2006.01) | |
| *C07K 16/18* | (2006.01) | |
| *C07K 16/28* | (2006.01) | |
| *A61K 39/00* | (2006.01) | |

(52) U.S. Cl.
CPC ...... *C07K 16/2896* (2013.01); *C07K 16/2827* (2013.01); *A61K 2039/505* (2013.01); *C07K 2317/55* (2013.01); *C07K 2317/74* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

2009/0217401 A1 * 8/2009 Korman et al. ................ 800/18

FOREIGN PATENT DOCUMENTS

WO 2007/005874 1/2007

OTHER PUBLICATIONS

Kyi et al. (2014, FEBS Lett. 588:368-376).*
Khoja et al. (2015, J. Immunother. Canc. 3:36-48).*
Henick et al., 2014, Expert Opinion on Therapeutic Targets 18:1407-1420.*
Ishida et al., 1992, EMBO J, 11:3887-3895.*
International Search Report and Written Opinion in PCT/EP2010/051563, dated Oct. 25, 2010.
Koehn et al., "PD-1-dependent mechanisms maintain peripheral tolerance of donor-reactive CD8(+) T cells to transplanted tissue," J. Immunol., 181(8):5313-5322 (2008).
Martin-Orozco et al., "Cutting edge: programed death (PD) ligand-1/PD-1 interaction is required for CD8(+) T cell tolerance to tissue antigens," J. Immunol., 177(12):8291-8295 (2006).
Ngo et al., The Protein Folding Problem and Tertiary Structure Prediction, Merz et al., eds., Birkhauser, Boston, pp. 492-495 (1994).
Paul, Fundamental Immunology, pp. 292-295 (1993).
Rudikoff et al., "Single amino acid substitution altering antigen-binding specificity," Proc. Natl. Acad. Sci. USA, 79:1979-1983 (1982).
Tokuriki et al., "Stability effects of mutations and protein evolvability," Curr. Opin. Struct. Biol., 19:596-604 (2009).
Wells, "Addivity of Mutational Effects in Proteins," Biochemistry, 29(37):8509-8517 (1990).
Williams et al., Development and characterization of monoclonal antibodies specific for the murine inhibitory FcγRIIB (CD32B), Eur. J. Immunol., 42:2109-2120 (2012).
Brian S. Henick, MD, Roy S. Herbst MD PhD & Sarah B. Goldberg MD MPH (2014), The PD-1 pathway as a therapeutic target to overcome immune escape mechanisms in cancer, Expert Opinion on Therapeutic Targets, 18:12, 1407-1420.

* cited by examiner

*Primary Examiner* — Elizabeth C Kemmerer
(74) *Attorney, Agent, or Firm* — Whitham, Curtis & Cook, P.C.

(57) ABSTRACT

The invention relates to PD-1 antibodies and PD-L1 antibodies and uses thereof.

5 Claims, 6 Drawing Sheets

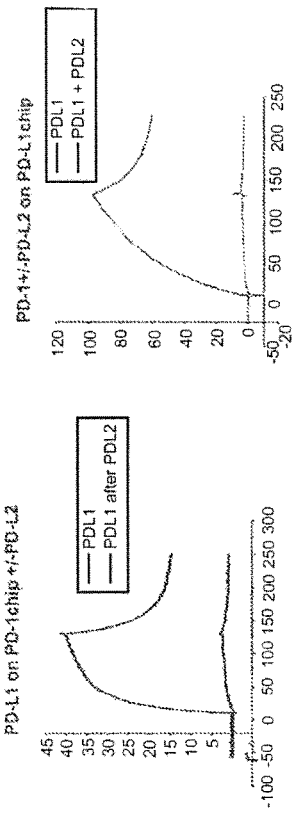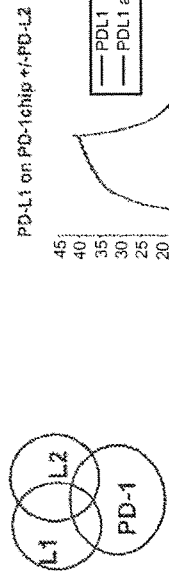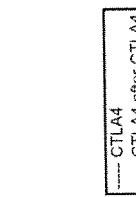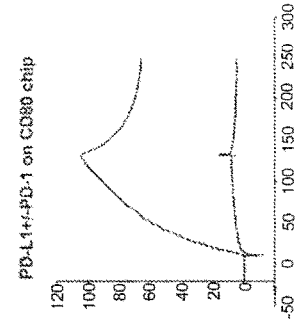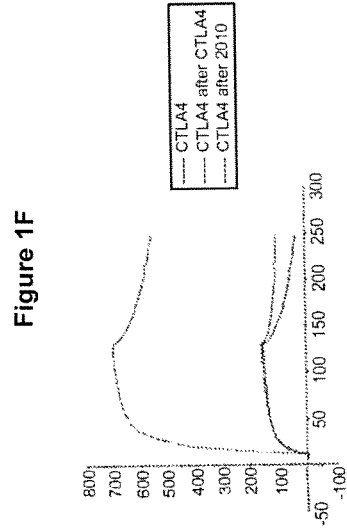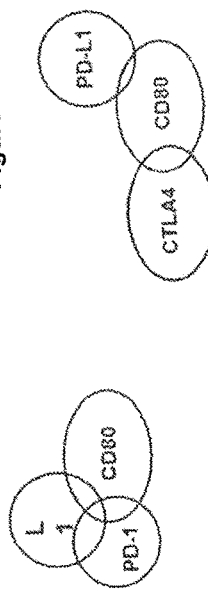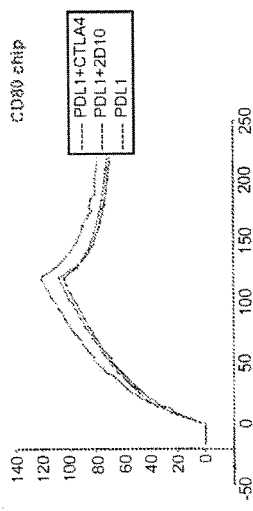
Figure 1A Figure 1B Figure 1C Figure 1D Figure 1E Figure 1F Figure 1G Figure 1H

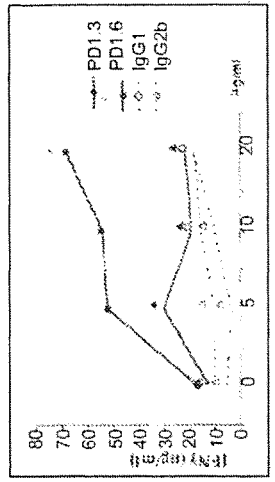
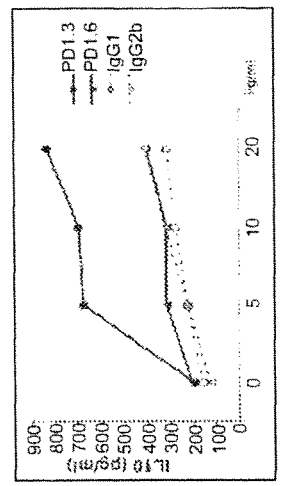
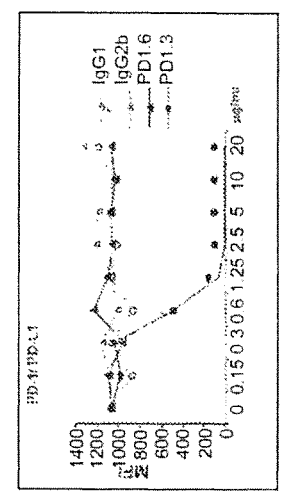
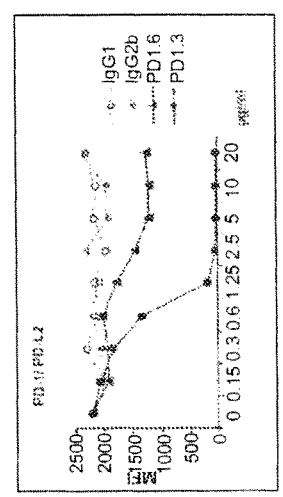
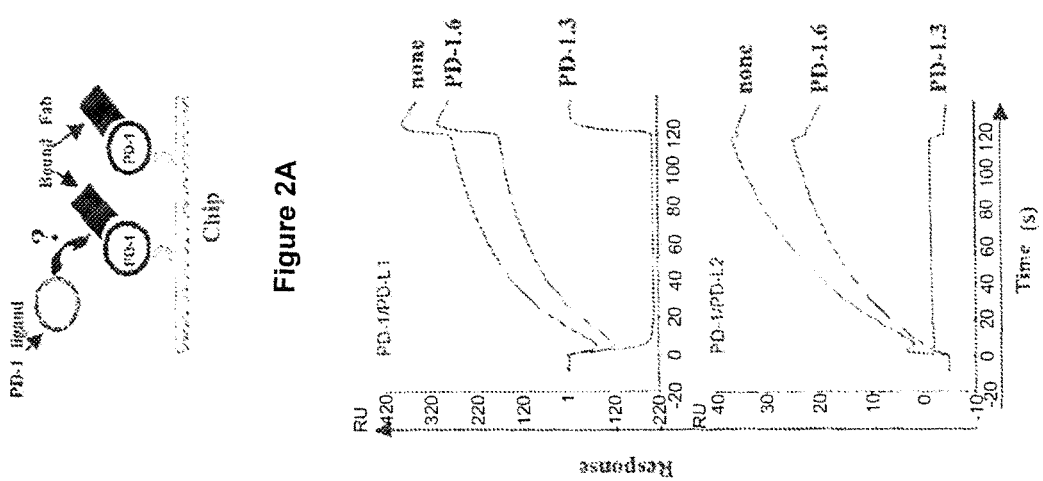
Figure 2A
Figure 2B
Figure 2C
Figure 2D
Figure 2E
Figure 2F

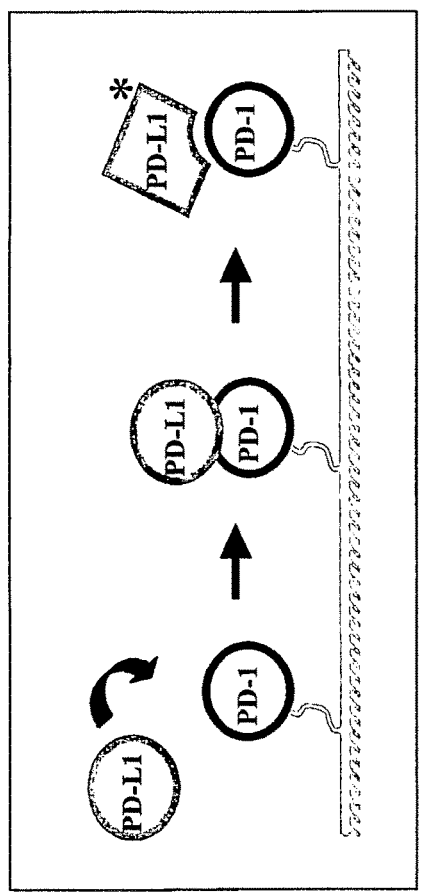
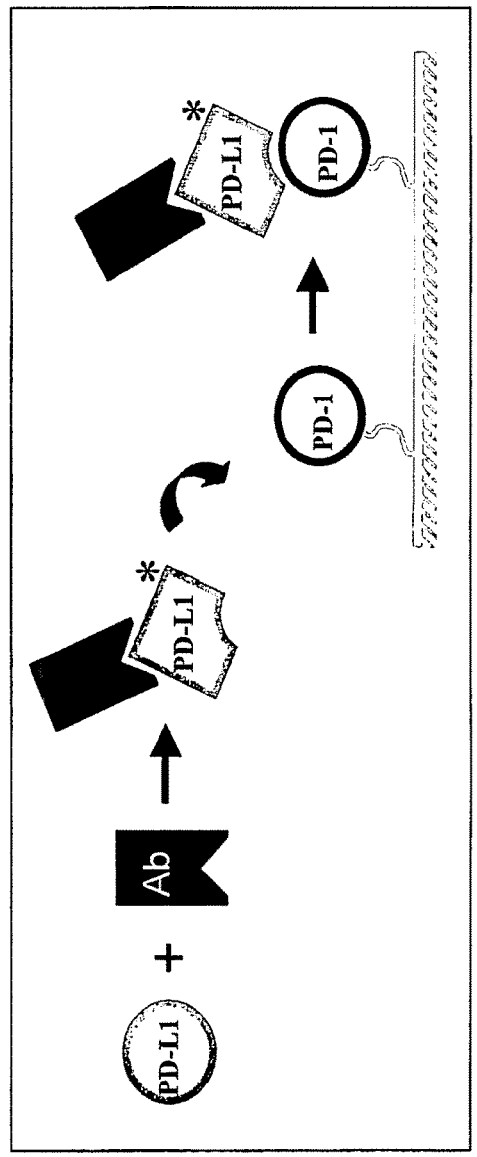
Figure 5A
Figure 5B

| Immobilized protein | Analyte | ka (x10⁴Ms⁻¹) | kd (x10⁻⁴s⁻¹) | ka2 (x10⁻⁴s⁻¹) | kd2 (x10⁻⁴s⁻¹) | K (x10⁷M⁻¹) | KD (nM) | KD#=1/K (nM) |
|---|---|---|---|---|---|---|---|---|
| PD-1 | PD-L2 | 8.44 | 11 | | | | 13 | |
| PD-1 | PD-L1 | 11 | 192 | 10.8 | 3.08 | 2.58 | | 38.8 |
| PD-L1 | PD-1 | 11.3 | 192 | 11.3 | 5.65 | 1.77 | | 56.5 | ka : association rate constant. kd : dissociation rate constant. ka2: forward rate constant for change of state. kd2: backward rate constant for change of state . KD=kd/ka : dissociation constant. K= (ka/kd)*(1+ka2/kd2): apparent affinity constant. KD# = 1/K: apparent dissociation constant.

Figure 6

SEQUENCE LISTING

<160> NUMBER OF SEQ ID NOS: 12

<210> SEQ ID NO 1
<211> LENGTH: 26
<212> TYPE: DNA
<213> ORGANISM: Artificial
<220> FEATURE:
<223> OTHER INFORMATION: primer

<400> SEQUENCE: 1
atgcagatcc cacaggcgcc ctggcc           26

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
tcagaggggc caagagcagt gtccatc          27

<210> SEQ ID NO 3
<211> LENGTH: 29
<212> TYPE: DNA
<213> ORGANISM: Artificial
<220> FEATURE:
<223> OTHER INFORMATION: primer

<400> SEQUENCE: 3
gcgaattcat gcagatccca caggcgccc        29

<210> SEQ ID NO 4
<211> LENGTH: 26
<212> TYPE: DNA
<213> ORGANISM: Artificial
<220> FEATURE:
<223> OTHER INFORMATION: primer

<400> SEQUENCE: 4
cttcccgtct tcacgggagc cggctg           26

<210> SEQ ID NO 5
<211> LENGTH: 27
<212> TYPE: DNA
<213> ORGANISM: Artificial
<220> FEATURE:
<223> OTHER INFORMATION: primer

<400> SEQUENCE: 5
atgaggatat tgctgtgtct tatattc          27

<210> SEQ ID NO 6
<211> LENGTH: 21

<212> TYPE: DNA
<213> ORGANISM: Artificial
<220> FEATURE:
<223> OTHER INFORMATION: primer

<400> SEQUENCE: 6
ttacgtctcc tccaaatgtg t                                    21

<210> SEQ ID NO 7
<211> LENGTH: 31
<212> TYPE: DNA
<213> ORGANISM: Artificial
<220> FEATURE:
<223> OTHER INFORMATION: primer

<400> SEQUENCE: 7
gcgaattcat gaggatattt gctgtctttta t                        31

<210> SEQ ID NO 8
<211> LENGTH: 31
<212> TYPE: DNA
<213> ORGANISM: Artificial
<220> FEATURE:
<223> OTHER INFORMATION: primer

<400> SEQUENCE: 8
ccggtacctt ctgggatgac caattcagct g                         31

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
acgccaaatt ttgagtgctt                                      20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
tgaaaagtgc aaatggcaag                                      20

<210> SEQ ID NO 11
<211> LENGTH: 32
<212> TYPE: DNA
<213> ORGANISM: Artificial
<220> FEATURE:
<223> OTHER INFORMATION: primer

<400> SEQUENCE: 11
gcgaattcat gatcttcctc ctgctaatgt tg                        32

<210> SEQ ID NO 12
<211> LENGTH: 29
<212> TYPE: DNA
<213> ORGANISM: Artificial

```
<220> FEATURE:
<223> OTHER INFORMATION: primer

<400> SEQUENCE: 12
ccggtaccgt caatgctggc caaagtaag                                            29
```

PD-1 ANTIBODIES AND PD-L1 ANTIBODIES AND USES THEREOF

RELATED APPLICATIONS

This application is a divisional application of U.S. patent application Ser. No. 13/148,420, filed Nov. 2, 2011, and now granted as U.S. Pat. No. 8,741,295, which is a National Stage entry of International Patent Application No. PCT/EP2010/051563, which was filed Feb. 9, 2010, and claims priority to European Patent Application No. 09305119.1, which was filed on Feb. 9, 2009, all of which are incorporated herein by reference in their entireties.

FIELD OF THE INVENTION

The invention relates to PD-1 antibodies and PD-L1 antibodies and uses thereof.

BACKGROUND OF THE INVENTION

Co-receptor signalling is an important mechanism for coordinating and tightly regulating immune responses. The usual scheme of activation of αβ T cells relies on positive signals given by peptide antigens presented by HLA class I or II. Co-receptor signals will either increase or prevent this activation.

Among the negative signalling molecules, those belonging to CD28/B7 families are by far the most studied. Three members of this family have been described: CTL-associated antigen-4 (CTLA-4), programmed death-1 (PD-1) and B and T lymphocyte attenuator (BTLA). They all play a role in the control of tolerance. They provide negative signals that limit, terminate and/or attenuate immune responses.

PD-1 was isolated as a gene up-regulated in a T cell hybridoma undergoing apoptosis and was named program death 1. PD-1 or CD279 is expressed on activated T and B cells as well as on activated myeloid cells.

Its expression is broader than CTLA-4 which is only found on activated T cells.

Upon coligation with the T cell Receptor (TcR), PD-1 elicits inhibitory signals.

The PD-1 cytoplasmic domain contains two tyrosines, one that constitutes an immunoreceptor tyrosine inhibitory receptor (ITIM) and the other one an immunoreceptor tyrosine based switch motif (ITSM). The phosphorylation of the second tyrosine leads to the recruitment of the tyrosine phosphatases SHP2 and to some extent SHP1. These phosphatases will dephosphorylate ZAP70, CD3ζ and PKC θ and consequently will attenuate T cell signals.

PD-1 mainly inhibits T and B cell proliferation by causing cell arrest in G0/G1 and inhibiting cytokine production in T cells.

Two PD-1 ligands have been described, PD-L1/B7H1/CD274 and PD-L2/B7-DC/CD273. PD-L1 is expressed at low levels on immune cells such as B cells, dendritic cells, macrophages and T cells and is up regulated following activation. PD-L1 is also expressed on non-lymphoid organs such as endothelial cells, heart, lung, pancreas, muscle, keratinocytes and placenta. The expression within non lymphoid tissues suggests that PD-L1 may regulate the function of self reactive T and B cells as well as myeloid cells in peripheral tissues or may regulate inflammatory responses in the target organs. PD-L1 expression is mainly regulated by type 1 and 2 interferon which are major regulators of PD-L1 on endothelial and epithelial cells. PD-L1 is expressed in tumor samples and is associated to poor prognosis. Various viral infections induce the intense PD-L1 expression on host tissues.

PD-L2/B7-DC cell surface expression is restricted to macrophages and dendritic cells, though PD-L2 transcript was found in non hematopietic tissues such as heart, liver and pancreas. Its surface expression depends on the production of IFNγ and Th2 cytokines.

PD-L1 and PD-L2 expression depends also on distinct stimuli. On macrophages PD-L1 is induced by INFγ whereas PD-L2 is induced by IL-4. A similar regulation is found on DC though these differences are not absolute. These studies tend to suggest that PD-L1 might regulate preferentially Th1 responses whereas PD-L2 would regulate Th2 responses.

Both PD-L1 and PD-L2 inhibit T cell proliferation, cytokine production and β1 and β2 integrins mediated adhesion. Although some contradictory data have proposed a costimulatory function. However, PD-L2 but not PD-L1 triggers reverse signalling in dendritic cells leading to IL-12 production and activation of T cells.

The expression patterns of PD-L1 and PD-L2 suggest both overlapping and differential roles in immune regulation. PD-L1 is abundant in a variety of human cancers (Dong et al (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100) Immune suppression can be reversed by inhibiting the local interaction of PD-1 with PD-L1, and the effect is additive when the interaction of PD-1 with PD-L2 is blocked as well (Iwai et al. (2002) Proc. Nat. 7. Acad. ScL USA 99: 12293-7; Brown et al. (2003) J. Immunol. 170:1257-66).

PD-1 deficient animals develop various autoimmune phenotypes, including autoimmune cardiomyopathy and a lupus-like syndrome with arthritis and nephritis (Nishimura et al. (1999) Immunity H: 141-51; Nishimura et al. (2001) Science 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) J Exp Med 198:71-78: Prokunina and Alarcon-Riquelme (2004) Hum Mol Genet. 13:R143; Nielsen et al. (2004) Lupus 11:510).

In animal models, PD-L1 and PD-L2 blockade using blocking mAbs evidence distinct roles in the susceptibility and chronic progression of experimental autoimmune encephalitis in a strain specific manner. In NOD prediabetic mice PD-L1 but not PD-L2 blockade precipitated diabetes. Using the RIP-mOVA mouse model of autoimmune diabetes, Martin-Orozco et al. found that PD-L1 but not PD-L2 mediated the inhibition of diabetes onset (Martin-Orozco et al. (2006) J. Immunol. 15; 177(12):8291-5).

To date, no satisfactory approach has been proven to induce potent immune responses against vaccines, especially in cancer patients. Methods have yet to be devised to overcome the immunosuppressive mechanisms observed in cancer patients, and during chronic infections.

Treatment of autoimmune diseases and prevention of transplantation rejection in graft versus host diseases (GVHD) depends on immunosuppressive agents that have serious side effects, or are not always effective. New immunosuppressive agents are desired.

SUMMARY OF THE INVENTION

The present invention relates to a PD-1 antibody (PD1.3) which is obtainable from the hybridoma accessible under CNCM deposit number I-4122.

The invention also relates to a PD-1 antibody which comprises the CDRs of PD1.3.

The invention relates to PD1.3 or a derivative thereof for the use in a method for treatment of the human or animal body by therapy.

The invention relates to PD1.3 or a derivative thereof for the treatment of a cancer or a chronic infection.

The invention relates to a vaccine for the treatment of a cancer or a chronic infection comprising PD1.3 or a derivative thereof.

The invention relates to a kit for the treatment of a cancer or a chronic infection comprising:
 a) PD1.3 or a derivative thereof; and
 b) a vaccine for the treatment of a cancer or a chronic infection.

The present invention also relates to a PD-L1 antibody, which stabilizes the binding of PD-L1 to PD-1.

The invention relates to a PD-L1 antibody, which stabilizes the binding of PD-L1 to PD-1 for the use in a method for treatment of the human or animal body by therapy.

The invention relates to a PD-L1 antibody, which stabilizes the binding of PD-L1 to PD-1 for the treatment of an autoimmune disease, transplantation rejection or a graft versus host disease.

BRIEF DESCRIPTION OF THE DRAWINGS

FIG. 1A-D depicts SPR analysis using Biacore of PD-L1 and PD-L2 competitive binding to PD-1. (A) A schematic representation of the surface competitive binding inhibition used in (B). (B) and (C). (B) The PD-1 chips were pre-incubated with increasing amount of PD-L2 (from 0 to 1000 RU) and PD-L1 were injected at 10 µg/ml for 2 minutes at a flow rate of 10 µl/min without removing bound PD-L2. Sensorgrams showing the PD-L1 binding at different level of PD-L2 occupancy are superimposed. (C) PD-1 recombinant proteins at 10 µg/ml were pre-incubated with increasing concentrations of PD-L2 (from 0 to 60 µg/ml) and injected for 2 minutes at a flow rate of 10 µl/min onto the PD-L1 chip. RU values monitored 10 seconds after the end of injection were plotted as a function of PD-L2 concentration (log scale). (D) and (E) Schematic representations of the solution inhibition used in (F)-(H), which show similar experiments done using CD80 protein (F) and CTLA-4 protein (G) and (H).

FIG. 2A-F shows that the PD1.3 antibody blocks the binding of PD-1 to both PD-L1 and PD-L2 and enhance T cell activation. (A) A schematic representation of the surface competitive binding inhibition used in (B), (C) and (D). In a first step the immobilized PD-1 proteins are saturated using the antibody Fabs and the corresponding PD-1 ligands are injected as a soluble analyte in a second step. (B and C); PD-L1Ig (B, top panel and C) and PD-L2Ig proteins (B, bottom panel and D) were injected at 10 µg/ml for two minutes at a flow rate of 10 µl/min onto PD-1 chip (none), or PD-1 chip pre-incubated with anti PD-1 Fab, PD1.3 or PD1.6. Sensorgrams showing the binding of the PD-1 ligands in the different situations are superimposed. The data shown are representative of two separate experiments. PD1.3 mAbs prevent PD-L1 Fc and PD-L2 Fc binding to cells expressing PD-1. (E and F) The PD1.3 mAb is able to induce the IFN-γ and IL10 production in CD4 T cells upon DC interaction. Allogenic iDC were cocultured with CD4+ T cells with anti-PD1.3, PD1.6 or isotype control. Cultures were incubated for 5 days, supernatants were removed for cytokine analysis. The levels of IFN-γ production (E) and IL10 production (F) were determined in duplicate by ELISA detection. The data shown are representative of two separate experiments.

FIG. 5 depicts likely mechanisms of interaction of PD-L1 with PD-1.

FIG. 6 Binding of PD-L1 and PD-L2 to immobilized PD-1 and binding of PD-1 to immobilized PD-L1, shown in tabular form.

DETAILED DESCRIPTION OF THE INVENTION

Definitions

Figure 3A:
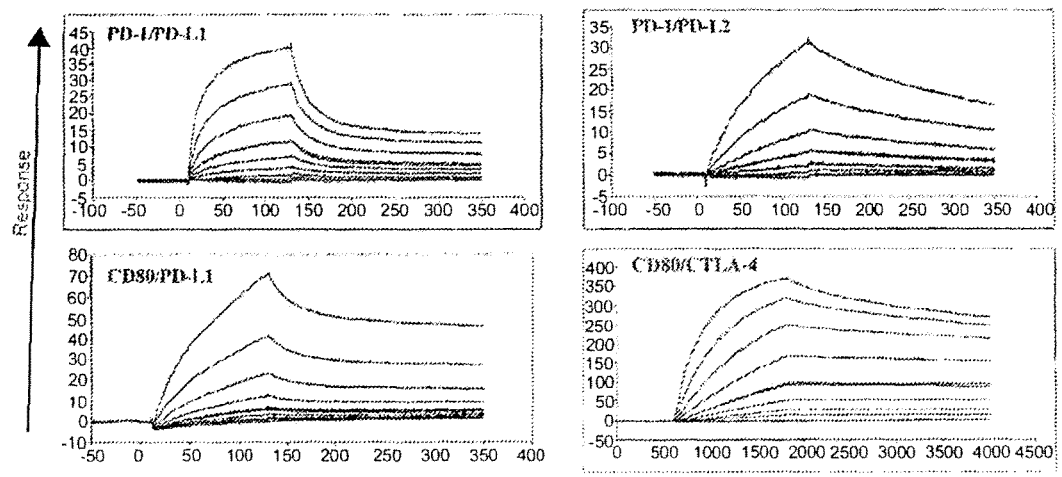
FIGS. 3 A and B shows that PD-L1 and PD-L2 do not bind to PD-1 with the same molecular mechanism. (A) Superimposed sensorgrams representative of PD-L1 and PD-L2 binding to PD-1 chip PD-L1 and CTLA-4 binding to CD80 chip. Proteins at 10 µg/ml were injected for thirty seconds at a flow rate of 10 µl/min onto PD-1 chip and allowed to dissociate for 120 more seconds. (B) Superimposed sensorgrams showing short (blue) and long (red) injections of PD-L1 (up) and PD-L2 (down) onto PD-1 chip respectively. Proteins at 10 µg/ml were injected for one or seven minutes at a flow rate of 10 µl/min onto the PD-1 chip. Sensorgrams were normalized in the Y axis and aligned in the X axis at the end of injection.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments or derivatives. Antibody fragments include but are not limited to Fv, Fab, F(ab')$_2$, Fab', dsFv, scFv, sc(Fv)$_2$ and diabodies.

In natural antibodies, two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHE CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementary Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The terms "chimeric antibody" refer to a genetically engineered fusion of parts of an animal antibody, typically a mouse antibody, with parts of a human antibody. Generally, chimeric antibodies contain approximately 33% mouse protein and 67% human protein. Developed to reduce the Human Anti-animal Antibodies response elicited by animal antibodies, they combine the specificity of the animal antibody with the efficient human immune system interaction of a human antibody.

According to the invention, the term "humanized antibody" refers to an antibody having variable region framework and constant regions from a human antibody but retains the CDRs of the animal antibody.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')$_2$.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)$_2$.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to a polypeptide (i.e. an antibody according to the invention) or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

In the context of the invention, the term "treating" or "treatment", as used herein, means reversing, alleviating, inhibiting the progress of, or preventing the disorder or condition to which such term applies, or one or more symptoms of such disorder or condition. A "therapeutically effective amount" is intended for a minimal amount of active agent which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used herein, the term "prevention" refers to preventing the disease or condition from occurring in a subject which has not yet been diagnosed as having it.

As used herein, the term "subject" denotes a mammal, such as a rodent, a feline, a canine, and a primate. Preferably a subject according to the invention is a human.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The inventors have deposited a murine PD-1 antibody (PD1.3) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on Feb. 4, 2009. The deposited hybridoma has CNCM deposit number I-4122.

"PD1.3" refers to an isolated PD-1 antibody which is obtainable from the hybridoma accessible under CNCM deposit number I-4122

The expression "a derivative of PD1.3" refers to a PD-1 antibody which comprises the 6 CDRs of PD1.3.

The inventors have deposited a murine PD-L1 antibody (PDL1.1) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on Oct. 15, 2008. The deposited hybridoma has CNCM deposit number I-4080.

"PDL1.1" refers to an isolated PD-L1 antibody which is obtainable from the hybridoma accessible under CNCM deposit number I-4080.

The expression "a derivative of PDL1.1" refers to a PD-L1 antibody which comprises the 6 CDRs of PDL1.1.

The inventors have deposited a murine PD-L1 antibody (PDL1.2) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on Oct. 15, 2008. The deposited hybridoma has CNCM deposit number I-4081.

"PDL1.2" refers to an isolated PD-L1 antibody which is obtainable from the hybridoma accessible under CNCM deposit number I-4081.

The expression "a derivative of PDL1.2" refers to a PD-L1 antibody which comprises the 6 CDRs of PDL1.2.

Antibodies of the Invention and Nucleic Acids Encoding them

The present invention relates to an isolated PD-1 antibody (PD1.3) which is obtainable from the hybridoma accessible under CNCM deposit number I-4122.

The present invention relates to the hybridoma accessible under CNCM deposit number I-4122.

The invention relates to an antibody which comprises the 6 CDRs of PD1.3.

In another embodiment, the invention relates to a derivative of PD1.3 which comprises the VL chain and the VH chain of PD1.3.

In another embodiment, the invention relates to a derivative of PD1.3 which is a chimeric antibody, which comprises the variable domains of PD1.3.

The present invention also relates to an isolated PD-L1 antibody, which stabilizes the binding of PD-L1 to PD-1.

Typically the stabilization of binding of PD-L1 to PD-1 may be measured according to the method described in the example.

Examples of isolated PD-L1 antibodies, which stabilize the binding of PD-L1 to PD-1 are PDL1.1, PDL1.2 or derivatives thereof.

The present invention also relates to the hybridomas accessible under CNCM deposit number I-4080 or I-4081.

The invention also relates to an antibody which comprises the 6 CDRs of PDL1.1 or the 6 CDRs of PDL1.2.

In another embodiment, the invention relates to a derivative of PDL1.1 or PDL1.2 which comprises the VL chain and the VH chain of PDL1.1 or PDL1.2 respectively.

In another embodiment, the invention relates to a derivative of PDL1.1 or PDL1.2 which is a chimeric antibody, which comprises the variable domains of PDL1.1 or PDL1.2.

In an embodiment, an antibody of the invention is a monoclonal antibody.

In an embodiment, an antibody of the invention is a chimeric antibody.

In an embodiment, an antibody of the invention is a humanized antibody.

A further embodiment of the invention relates to a nucleic acid sequence encoding an antibody of the invention.

In a particular embodiment, the invention relates to a nucleic acid sequence encoding the VH domain or the VL domain of an antibody of the invention.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like.

Any expression vector for animal cell can be used, so long as a gene encoding the human antibody C region can be inserted and expressed. Examples of suitable vectors include pAGE107, pAGE103, pHSG274, pKCR, pSG1 beta d2-4- and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3x63-Ag8.653 cell (ATCC CRL1580), CHO cell in which a dihydrofolate reductase gene (hereinafter referred to as "DHFR gene") is defective, rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Methods of Producing Antibodies of the Invention

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of: (i) culturing a transformed host cell according to the invention under conditions suitable to allow expression of said antibody; and (ii) recovering the expressed antibody.

In another particular embodiment, the method comprises the steps of:
(i) culturing the hybridoma deposited as CNCM I-4122, CNCM I-4080 or CNCM I-4081 under conditions suitable to allow expression of the antibody; and
(ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like.

Methods for producing humanized antibodies based on conventional recombinant DNA and gene transfection techniques are well known in the art. Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with PD-1 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The $F(ab')_2$ of the present invention can be obtained treating an antibody which specifically reacts with PD1.3 with a protease, pepsin. Also, the F(ab')$_2$ can be produced by binding Fab' described below via a thioether bond or a disulfide bond.

The Fab' of the present invention can be obtained treating F(ab')$_2$ which specifically reacts with human PD-1 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further embodiment of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties.

It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as thoseof cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Enzymatic cleavage of carbohydrate moieties on antibodies can be achieved by the use of a variety of endo- and exo-glycosidases.

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. Nos. 4,640,835; 4,496, 689; 4,301, 144; 4,670, 417; 4,791, 192 or 4,179,337.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. J Exp Med. 1992 Oct. 1; 176(4):1191-5 and Shopes B. J. Immunol. 1992 May 1; 148(9):2918-22).

Therapeutic Uses of the Antibodies of the Invention

The inventors have demonstrated that PD1.3 inhibits the binding of PD-L1 and PD-L2 to PD-1 and thereby may be used to overcome the immunosuppressive mechanisms mediated by PD-1 observed in cancer patients and during chronic infections.

The invention relates to PD1.3 or a derivative thereof for the use in a method for treatment of the human or animal body by therapy.

The invention relates to PD1.3 or a derivative thereof for the treatment of a cancer or a chronic infection.

The invention also relates to a method for treating a cancer or a chronic infection wherein said method comprises the step of administering to a subject in need thereof a therapeutically effective amount of PD1.3 or of a derivative thereof.

Examples of cancers include, but are not limited to, hematological malignancies such as B-cell lymphoid neoplasm, T-cell lymphoid neoplasm, non-Hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm and myeloid cell lineage neoplasm. Examples of non-hematological cancers include, but are not limited to, colon cancer, breast cancer, lung cancer, brain cancer, prostate cancer, head and neck cancer, pancreatic cancer, bladder cancer, colorectal cancer, bone cancer, cervical cancer, liver cancer, oral cancer, esophageal cancer, thyroid cancer, kidney cancer, stomach cancer, testicular cancer and skin cancer.

Examples of chronic infections include, but are not limited to, viral, bacterial, parasitic or fungal infections such as chronic hepatitis, lung infections, lower respiratory tract infections, bronchitis, influenza, *pneumoniae* and sexually transmitted diseases. Examples of viral infections include include, but are not limited to, hepatitis (HAV, HBV, HCV), herpes simplex (HSV), herpes zoster, HPV, influenza (Flu), AIDS and AIDS related complex, chickenpox (varicella), common cold, cytomegalovirus (CMV) infection, smallpox (variola), colorado tick fever, dengue fever, ebola hemorrhagic fever, foot and mouth disease, lassa fever, measles, marburg hemorrhagic fever, infectious mononucleosis, mumps, norovirus, poliomyelitis, progressive multifocal leukencephalopathy (PML), rabies, rubella, SARS, viral encephalitis, viral gastroenteritis, viral meningitis, viral pneumonia, West Nile disease and yellow fever. Examples of bacterial infections include include, but are not limited to, pneumonia, bacterial meningitis, cholera, diphtheria, tuberculosis, anthrax, botulism, brucellosis, campylobacteriosis, typhus, gonorrhea, listeriosis, lyme disease, rheumatic fever, pertussis (Whooping Cough), plague, salmonellosis, scarlet fever, shigellosis, syphilis, tetanus, trachoma, tularemia, typhoid fever, and urinary tract infections. Examples of parasitic infections include include, but are not limited to, malaria, leishmaniasis, trypanosomiasis, chagas disease, cryptosporidiosis, fascioliasis, filariasis, amebic infections, giardiasis, pinworm infection, schistosomiasis, taeniasis, toxoplasmosis, trichinellosis, and trypanosomiasis. Examples of fungal infections include include, but are not limited to, candidiasis, aspergillosis, coccidioidomycosis, cryptococcosis, histoplasmosis and tinea pedis.

PD1.3 or a derivative thereof may be used as a vaccine adjuvant for the treatment of a cancer or a chronic infection.

The invention relates to a vaccine for the treatment of a cancer or a chronic infection comprising PD1.3 or a derivative thereof.

The invention relates to a kit for the treatment of a cancer or a chronic infection comprising:
a) PD1.3 or a derivative thereof; and
b) a vaccine for the treatment of a cancer or a chronic infection.

The two elements of the kit may be administered concomitantly or sequentially over time.

Examples of vaccine for the treatment of a cancer or a chronic infection are: include, but are not limited to vaccines against viral, bacterial, parasitic or fungal infections such as HIV and HBV and vaccines against viral associated cancers (for instance HPV or HBV) or anti cancer vaccines for instance used to treat patients with melanoma, leukemia, breast cancers, lung cancers.

Furthermore, the inventors have generated PD-L1 antibodies, which stabilize the binding of PD-L1 to PD-1 and thereby may be used to stimulate the immunosuppressive mechanisms mediated by PD-1. These PD-L1 antibodies may be used as immunosuppressive agents.

In a further embodiment, the invention relates to a PD-L1 antibody, which stabilizes the binding of PD-L1 to PD-1 for the use in a method for treatment of the human or animal body by therapy.

In particular, the invention relates to a PD-L1 antibody, which stabilizes the binding of PD-L1 to PD-1 for the treatment of an autoimmune disease, transplantation rejection or a graft versus host disease.

The invention also relates to a method for treating an autoimmune disease, transplantation rejection or a graft versus host disease, wherein said method comprises the step of administering to a subject in need thereof a therapeutically effective amount of PD-L1 antibody, which stabilizes the binding of PD-L1 to PD-1.

Typically the PD-L1 antibodies, which stabilize the binding of PD-L1 to PD-1 may be PDL1.1, a derivative thereof, PDL1.2 or a derivative thereof.

Examples of autoimmune diseases which may be treated include but are not limited to rheumatoid arthritis (RA), insulin dependent diabetes mellitus (Type 1 diabetes), multiple sclerosis (MS), Crohn's disease, systemic lupus erythematosus (SLE), scleroderma, Sjögren's syndrome, pemphigus vulgaris, pemphigoid, addison's disease, ankylosing spondylitis, aplastic anemia, autoimmune hemolytic anemia, autoimmune hepatitis, coeliac disease, dermatomyositis, Goodpasture's syndrome, Graves' disease, Guillain-Barré syndrome, Hashimoto's disease, idiopathic leucopenia, idiopathic thrombocytopenic purpura, male infertility, mixed connective tissue disease, myasthenia gravis, pernicious anemia, phacogenic uveitis, primary biliary cirrhosis, primary myxoedema, Reiter's syndrome, stiff man syndrome, thyrotoxicosis, ulceritive colitis, and Wegener's granulomatosis.

Typically a PD-L1 antibody, which stabilizes the binding of PD-L1 to PD-1 may be used in combination with other immunosuppressive and chemotherapeutic agents such as, but not limited to, prednisone, azathioprine, cyclosporin, methotrexate, and cyclophosphamide.

The invention also relates to pharmaceutical composition comprising an antibody of the invention.

Therefore, an antibody of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention will further be illustrated in view of the figures and example.

EXAMPLE

Abstract

The programmed death 1 molecule (PD-1) is involved in peripheral tolerance and in the regulation of persistent viral infections as well as a mechanism of tumor escape from the immune system. Two ligands, PD-L1 and PD-L2 have been described that differ in tissue distribution, regulation of expression and residues involved in their binding to PD-1. We have further investigated the molecular mechanisms of PD-1 interactions with its ligands using recombinant proteins and mAbs by surface plasmon resonance and cell surface binding. We could demonstrate that both PD-L1 and PD-L2 cross-compete for PD-1 binding. Interestingly and along the same line, one selected PD-1 mAb could interfere with the binding of both PD-L1 and PD-L2. PD-L1 and PD-L2 bound PD-1 with comparable affinities but striking differences standed at the level of the association and dissociation characteristics. Hence, PD-L1 but not PD-L2 had a delayed interaction reminiscent of a phenomenom of conformational transition. These mechanisms were further confirmed thanks to PD-L1 mAbs that could delay the dissociation of PD-L1 from PD-1. This mechanism was not restricted to PD-1 interaction since PD-L1 behaves in a similar manner with its second ligand CD80.

Finally, CTLA-4 and PD-L1 bound to distinct, non overlapping sites on CD80. These data further emphasize the differential molecular mechanisms of interaction of both ligands to PD-1 that identify new avenues to devise mAb therapy that could prevent the binding of both ligands to PD-1 to permit an optimal blockade of immune inhibition in chronic infection, cancer and transplantation.

Materials and Methods

Constructs

Human PD-1 and CTLA-4 cDNA was generated by RT-PCR from (CD3+CD28)-activated T cells using primers shown in Table 1 and subsequently subcloned into a DNA4 vector (Yang W C et al., Int. Immunol 2000). The extracellular region of human PD-1 and CTLA-4 (aa 1 to 152 and aa) were amplified from this plasmid using primers shown in Table 1 and cloned in frame with the Fc fragment of the human IgG1 sequence using the Cos Fc Link vector (SmithKline Beecham Pharmaceuticals, King of Prussia, Pa.). Human PD-L1 and PD-L2 cDNAs were generated by RT-PCR from brain and lung human total RNA (Clontech Laboratories, Inc) respectively using primers shown in Table 1. The same cloning protocol as PD-1 has been used to generate the full-length PD-Ls and their extracellular portions as Ig fusion proteins.

TABLE 1

Primer sequences used in this study

| Name | Primers | Sequences |
|---|---|---|
| PD1 Full length | Sens | ATGCAGATCCCACAGGCGCCCTGGCC (SEQ ID NO: 1) |
|  | antisense | TCAGAGGGGCCAAGAGCAGTGTCCATC (SEQ ID NO: 2) |
| PD1 Extra-cellular | sens | GCGAATTCATGCAGATCCCACAGGCGCC (SEQ ID NO: 3) |
|  | antisense | CTTCCCGTCTTCACGGGAGCCGGCTG (SEQ ID NO: 4) |
| PD-L1 Full length | sens | ATGAGGATATTTGCTGTCTTTATATTC (SEQ ID NO: 5) |
|  | antisense | TTACGTCTCCTCCAAATGTGT (SEQ ID NO: 6) |
| PD-L1 Extra-cellular | sens | GCGAATTCATGAGGATATTTGCTGTCTTTAT (SEQ ID NO: 7) |
|  | antisense | CCGGTACCTTCTGGGATGACCAATTCAGCTG (SEQ ID NO: 8) |
| PD-L2 Full length | sens | ACGCCAAATTTTGAGTGCTT (SEQ ID NO: 9) |
|  | antisense | TGAAAAGTGCAAATGGCAAG (SEQ ID NO: 10) |
| PD-L2 Extra-cellular | sens | GCGAATTCATGATCTTCCTCCTGCTAATGTTG (SEQ ID NO: 11) |
|  | antisense | CCGGTACCGTCAATGCTGGCCAAAGTAAG (SEQ ID NO: 12) |

PD1, PD-L, PD-L2, CTLA-4 and CD80 Soluble Human Ig Fusion Proteins

The chimeric cDNA were constructed by ligating the extra-cellular domain of PD1, PD-L1, PD-L2 and CTLA-4 with the Fc fragment of the human IgG1 sequence using the Cos Fc Link vector.

Cos cells were cultured in DMEM 10% FBS with 2 mM L-Glutamine and transfected in CHO-S-SFM II medium (from Invitrogen) without FBS with DNA plasmid construct in CFL vector with FuGENE 6 Transfection reagent according to the manufacturer's protocol (ROCHE). The culture supernatant were collected seven days after transfection, filtered and loaded on a 5-ml Affigel protein A column according to the manufacturer's protocol (Bio-rad, Hercules, Calif.). After washing, the proteins were eluted with a 0.1 mol/L citrate buffer, pH 3.5, concentrated, and dialyzed against phosphate-buffer saline (PBS). Purification steps were monitored by ELISA using a sandwich revelation system composed with coated antibody against human IgG-UNLB and humain IgG-AP (Southern Biotechnology Associates) and revealed by pNPP substrat (Sigma). Purity and quality of the human Ig fusion proteins were controlled by gel electrophoresis and by cell surface staining on human PD1, PD-L1, PD-L2 or CTLA-4 transfected COS cells line respectively. CD80 Fc was purchased from R&D.

Generation of Anti-Human PD1, PD-L1, PD-L2 and CD80 Monoclonal Antibody and Fab Fragmentation MAbs to human PD1, PD-L1 and PD-L2 were produced similarly. Female BALB/c mice were immunised by IP injection with 10 μg of human Ig fusion protein with Freund adjuvant Immunisation was repeated three times at 2 weeks intervals, the fourth immunisation was made by IV injecting with 10 μg of Ig fusion protein in the codal tail. Three days later spleen cells were fused with X63Ag8 myeloma cells with PEG 1500 (Roche) and cloned with HAT selection (Sigma) and Hybridoma cloning factor (HCF from Origen). The hybridoma supernatants were screened by cell surface staining human PD1, PD-L1 or PD-L2 transfected COS cells line respectively and for lack of reactivity with untransfected COS cells. Clones PD1.3 (mouse, IgG2b) and PD1.6 (mouse, IgG1), PDL1.1, PDL1.2 and PDL1.3 (mice, IgG1) and PD-L2 (mouse, IgG1) were produced by liquid ascitis production, purified with protein A affinity column and chosen as reagents for FACS and Biacore analysis and functional studies. The transitory transfect COS cells were obtained with FuGENE 6 Transfection reagent according to the manufacturer's protocol (ROCHE). CD80 mAb 2D10.4 as been previously reported.

Fab fragmentation was performed using papain with ImmunoPure Fab Preparation Kit according to the manufacturer's protocol (PIERCE). MAbs whole and Fab were subjected to reducing SDS-PAGE and the gel was staining with Coomassie blue, no contaminating whole mAb was present in the Fab preparation (data not shown). Fab retained their capacity to bind to the respectively receptors. FACS analysis with whole mAbs and their Fab revealed approximately the same mean fluorescence intensity upon binding to PD-1, PD-L1 or PD-L2 transfected COS cells.

FACS Analysis

Cos-7 cell line was cultured in DMEM 10% FBS with 2 mM of L-Glutamine (Invitrogen). The staining of transiently transfected COS cells followed the basic procedure. Briefly, cells were incubated with optimized dilution of the mAbs, were washed in cold PBS with 2% FBS and 0.02% sodium azide and incubated with goat anti mouse (GAM) conjugated with FITC (Beckman Coulter). After washes, cells were analyzed on a FACS CANTO flow cytometer (Becton Dickinson).

To test the effect of PDL1.1 and PDL1.2 anti-PD-L1 non blocking antibodies on the binding of PD-L1 to PD-1, 4 μg/ml of PD-1 Ig protein were added on PD-L1 tranfected COS cells untreated or preincubated for 5 or 30 minutes with 7.5 μg/ml of PDL1.1, PDL1.2 or PDL1.3 Fabs mAbs. The binding of PD-1 Ig was revealed with Goat anti human (GAH) conjugated PE. The results are expressed as mean fluorescence intensity (MFI). The MR ratio was calculated by the MFI of Fab preincubated cells/MFI of untreated cells.

Biacore Experiments

Surface plasmon resonance measurements were performed on a Biacore 1000 upgrade apparatus (Biacore GE Healthcare) at 25° C. In all Biacore experiments HBS-EP buffer (Biacore GE Healthcare) served as running buffer and sensorgrams were analyzed with Biaevaluation 4.1 software.

For protein immobilization, recombinant proteins were immobilized covalently to carboxyl groups in the dextran layer on a Sensor Chip CM5. The sensor chip surface was activated with EDC/NHS (N-ethyl-N'-(3-dimethylamino-propyl) carbodiimidehydrochloride and N-hydroxysuccinimide (Biacore GE Healthcare)). Proteins were diluted to 10 μg/ml in coupling buffer (10 mM acetate, pH 5.2) and injected until the appropriate immobilization level was reached (i.e. 1000 to 1200 RU).

Deactivation of the remaining activated groups was performed using 100 mM ethanolamine pH 8 (Biacore GE Healthcare).

In order to determine the affinity of proteinsserial dilutions from 0.3 to 30 nanoM and from 1.37 to 90 nanoM of soluble antibodies and recombinant proteins respectively were injected for 2 min at a constant flow rate of 40 μl/min on dextran layers containing immobilized recombinant target proteins and allowed to dissociate for 3 min before regeneration by a eight second injection of 500 mM NaCl and 10 mM NaOH buffer.

The resulting sensorgrams were analysed by global fitting using the appropriate model.

For surface competitive binding inhibition experiments, the soluble analytes were injected at a constant concentration of 10 µg/ml on dextran layers containing appropriate immobilized recombinant target proteins. Each competition cycle consisted of three injection steps of 2 min at 10 µl/min constant flow rate. Firstly, one analyte is injected twice. Secondly, without removing the first analyte, a second analyte is injected and sensorgrams and RU values are monitored. Second analyte sensorgram is compared to the sensorgram obtained when this analyte is injected directly on nude recombinant target proteins. Percentage of second analyte binding inhibition by first analyte ($I_{2-1}$) was determined from RU values obtained 10 second after the end of injections, using the following formula: $I_{2-1}=(1-(RU_{2-1}/RU_2))*100$. $RU_{2-1}$ and $RU_2$ are second analyte RU values monitored in the presence and in the absence of first analyte respectively. After each cycle, Sensorchips were regenerated by eight second injection of 500 mM NaCl and 10 mM NaOH buffer at flow rate of 40 µl/min.

For solution inhibition experiments, the soluble recombinant proteins at a constant concentration of 10 µg/ml were pre-incubated with increasing concentrations of cognate recombinant ligands (from 0 to 60 µg/ml) or antibodies (from 0 to 80 µg/ml and 0 to 120 µg/ml for PD-1 mAbs, PD-L2 mAbs and PD-L1 mAbs respectively) and injected for 2 minutes at a flow rate of 10 µl/min onto the appropriate chips. RU values were monitored 10 seconds after the end of injection. After each cycle, Sensorchips were regenerated by eight second injection of 500 mM NaCl and 10 mM NaOH buffer at flow rate of 40 µl/min.

To measure the stabilization effect of PDL1.1 and PDL1.2 antibodies on PD-L1 binding to PD-1, the soluble recombinant PD-L1 Ig proteins at a constant concentration of 10 µg/ml were pre-incubated with a saturating concentration of 100 µg/ml of PDL1.1 and PDL1.2 antibody Fabs and injected for 10 minutes at a flow rate of 10 µl/min onto the PD-1 chips. The sensorgrams were monitored, normalized to 100 RU in the Y axis and compared to those obtained without pre-incubation with anti-PD-L1 antibody Fabs.

Preparation of Immature Monocyte-Derived DCs (iDC)

iDCs were prepared from monocytes according to previously established protocols (Charbonnier et al, Eur J. Immunol. 1999; 29(8):2567-78) with modifications. PBMC were obtained from healthy individual volunteers and isolated by fractionation over Lymphoprep™ Axis-Shield (ABCys) gradient centrifugation. Monocytes were obtained from PBMC by negative selection with a Monocyte Isolation Kit II human according to the manufacturer's protocol (Miltenyi Biotec). Monocytes were cultured in 6-well plates at $2.5\times10^6$ cells/well (Falcon, BD Biosciences) in RPMI 1640 (Invitrogen) medium containing 10% FBS and differentiated five days with 20 ng/ml of recombinant human Interleukin 4 (IL-4) and 100 ng/ml of recombinant human GM-CSF (ABCys French society). iDcs were consistently CD14 and CD83 neg, >92% CD1a, >96% CD11b, >80% HLADR, >20% CD80 cells.

Allogenic Stimulation of CD4+ T Cells with iDC

CD4+ T cells were isolated from PBMC with negative selection with CD4+ T Cell Isolation Kit II human according to the manufacturer's protocol (Miltenyi Biotec). CD4+ T cells were routinely >95% pure. CD4+ T cells ($2\times10^5$/well) were cocultured with $2\times10^4$ iDC/well in triplicate in 96-well flat-bottom plates (Falcon; BD Biosciences) in 200 µl of RPMI 1640 (Invitrogen) supplied with 10% FBS, with mAbs to PD-1, PD-L1 and PD-L2 at various concentration. Isotype matched mAbs (B9.3, mouse IgG1 and B9.4, mouse IgG2b) were used as negative controls. Cultures were incubated for 5 days.

ELISA for Cytokine Analysis

Supernatants were then collected, IFN-γ and IL10 production were detected in culture supernatants by ELISA detection using OptEIA™ human IFN-γ and IL10 Set according to the manufacturer's protocol (BD Biosciences). The limit of detection was 4 pg/ml.

Results

Characterization of PD-1, PD-L1, PD-L2 mAbs and PD-1 Ig, PD-L1 Ig and PD-L2 Ig Fusion Proteins In order to perform this study we have made mAbs directed against PD-1 and its ligands and used them as Fabs and soluble fusion proteins corresponding to extracellular domain of PD-1, PDL-1 and PDL-2 and the Fc portion of human IgG1. We investigated the binding characteristics of both Fab fragments of the mAbs and fusion proteins by SPR using a BiacoreT100 and flow cytometry on transfected cells (data not shown).

By kinetic analysis using SPR Fab fragments of mAbs KD ranged from 0.26 to 41 nM.

The two PD-1 mabs, PD1.3 and PD1.6 did not cross bind (data not shown). The three PD-L1 mAbs delineate two groups with PDL1.1 and PDL1.2 which cross bind on one hand whereas PDL1.3 epitope is independent of the two other mAbs (data not shown).

We next investigated whether PD-L1 and PD-L2 could bind to PD-1 coupled to CM5 chip and reciprocally. We observed that covalent coupling inactivates the PD-L2 recombinant protein and prevents PD-1 Fc and PD-L2 mAb binding (data not shown) indicating that the binding site probably contains free NH2, whereas it had no impact on PD-L1 and PD-L2 binding to immobilized PD-1 (FIG. 1, FIG. 6 and FIG. 4A) nor on PD-1 binding to immobilized PD-L1 (FIG. 1 and FIG. 6). Similar experiments were made using CD80 and CTLA-4 proteins.

Taken together, these results demonstrate that the three fusion proteins bound to their cognate receptors and Fabs fragments specifically bound to their target coupled to CM5 sensor chips.

PD-L1 and PD-L2 Cross Compete for PD-1 Binding

We next investigated whether PD-L1 and PD-L2 could bind together to PD-1 or cross-competed for PD-1 occupancy.

As shown in FIG. 1, we performed a SPR analysis. The PD-1 chips were pre-incubated with increasing amount of PD-L2 (from 0 to 1000 RU of bound PD-L2) and PD-L1 was injected without removing bound PD-L2. Sensorgrams show that PD-L1 can outcompete for PD-L2 upon increasing PD-L2 occupancy. (FIG. 1 panel A). In another experimental setting, we pre-incubated PD-1 recombinant proteins at 10 µg/ml with increasing concentrations of PD-L2 (from 0 to 60 µg/ml) and injected the complexes onto the PD-L1 chip. PD-L2 pre-incubation prevented PD-1 binding to PD-L1 in a dose dependent manner (FIG. 1, panel B).

These data demonstrate that both ligands prevent the binding of the other PD-1 ligand and that consequently the previous binding of PD-L1 or PD-L2 to PD-1 would prevent the interaction with the other ligand in a dose dependent manner. Same results were obtained by flow cytometry on transfected cells (data not shown). Human PD-L1 interacts with human CD80 (FIG. 1C). In order to analyze a possible interference of the binding of PD-L1 to CD80 in presence of PD-1, we performed pre-incubation experiments and show that pre-incubation of PD-L1 with PD-1 prevents PD-L1: CD80 interaction (FIG. 1C). We next tested the interaction of CD80 with CTLA-4 and PD-L1. As already reported, there is a strong binding of CD80 to CTLA4 that is prevented by CTLA-4 Ig itself but also the CD80 mAb 2D10.4 (FIG. 1E). Finally, we tested the interaction of CTLA-4 and PD-L1 with CD80 (FIG. 1D). The previous binding of CTLA-4 to CD80 does not prevent PD-L1 binding. The CD80 mAb 2D10.4 did not prevent PD-L1 binding to CD80 whereas it abrogated completely CTLA-4-CD80 interaction. These experiments demonstrate that CTLA-4 and PD-L1 can both bind at the same time with human PD-L1.

PD1.3 Mab Prevents the Binding of Both PD-L1 and PD-L2 to PD-1

In an additional set of experiments, we investigated whether PD-1 mAbs could in a reverse way prevent the binding of both PD-L1 and PD-L2. As shown in FIG. 2 panels B and C, anti-PD1.3 but not anti-PD1.6 completely inhibited the binding of both PD-L1 (FIGS. 2B and 2C upper panels) and PD-L2 (FIGS. 2B and 2C lower panels) to PD-1. In a reciprocal manner, PD1.3 mAb blocked in a dose dependent way the binding of PD-1 Fc to PD-L1 chips (data not shown). By FACS analysis, PD1.3 mAb can inhibit PD-1 Fc binding to PD-L1 and PD-L2 expressing cells (FIG. 2C). PD-1 Mabs can Modulate T Cell Activation by Allogeneic Immature Dendritic Cells We next investigated the functional capabilities of the mAbs directed against PD-1. We tested their ability to induce the activation allogeneic T cells against a suboptimal activation namely immature monocytes derived dendritic cells. The mAb inhibiting PD-1 ligand interaction, PD1.3 but not the non inhibitory PD1.6 was able to enhance the activation of CD4 T cells as indicated by an increased INFγ and IL10 production (FIG. 2 panels D) and T cell proliferation (data not shown).

Altogether, these data demonstrate that the two ligands compete for PD-1 binding and conversely that an inhibitory anti-PD-1 mAb can readily prevent PD-1 ligands binding and as consequence enhance T cell activation.

PD-L1 and PD-L2 Differ in their Molecular Mechanisms of PD-1 Binding

We next investigated the mechanisms of PD-L1 and PD-L2 binding to PD-1. To pinpoint the different steps of this interaction we performed a careful kinetic study. Kinetic binding assays were performed to determine the equilibrium dissociation constant between PD-1 and PD-L1 and PD-L2 fusion proteins. The binding data were first analyzed using the 1:1 Langmuir model. For PD-L2/PD-1 the fitting was very good and yielded a KD of 9.97 nM. Though both recombinant analytes were bivalent the Langmuir model fitted very well to the data indicating that the two binding sites of each molecule probably interact at the same time. Thus, the KD value most likely represents an avidity value.

For PD-L1/PD-1, as well as PD-L1/CD80 fitting using the Langmuir model was very bad and inappropriate.

Indeed, as shown in FIG. 3 panel A, the two ligands interacted with PD-1 with distinct features. PD-L1 associated rapidly and dissociated also very fast. In contrast PD-L2 binding was delayed with a different slope and more robust. The residual values strongly differed. Hence, two distinct phenomenons were observed in the PDL-L1 PD-1 dissociation phase. An early phase, during which PD-L1 rapidly dissociated from PD-1 at the beginning of the dissociation, was followed by a latter phase characterized by a low dissociation rate with signals appearing more stable, whereas PD-L2 PD-1 dissociation was more homogeneous.

From the different models tested for fitting, the "conformational modification model" gave the best and reliable fit and yielded an apparent dissociation constant (KD#) of 10.7 nM and 56.5 nM on PD-1 chips.

It can be predicted from the "conformational modification model" that increasing the time of injection would also increase the stability of binding. To test this hypothesis we then compared the binding of PD-L1 and PD-L2 to PD-1 chips following two settings, 10 μg/ml PD-L1 or PD-L2 fusion proteins were injected during 7 or 1 minute respectively. The sensorgrams depicted in FIG. 3B clearly demonstrate that the contact time influence the stability of PD-L1 binding to the PD-1 chip. The dissociation of PD-L1 to the PD-1 chip was slower when the injection time was longer.

Figure 3B:
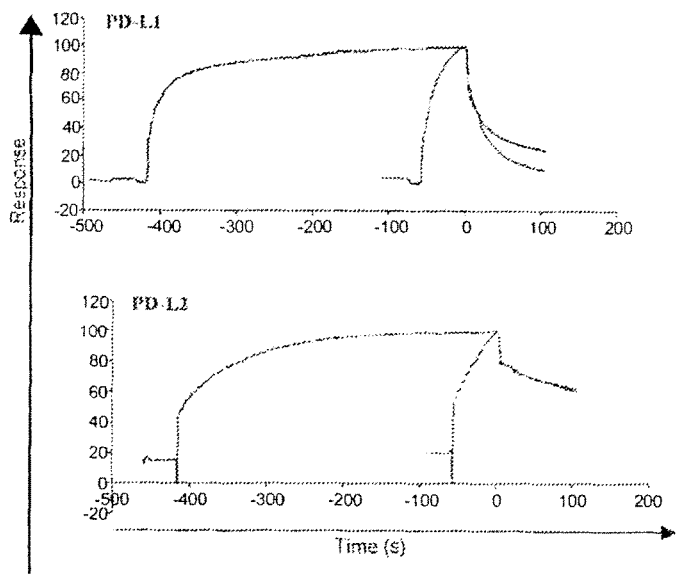

As a control, for PD-L2 the dissociation kinetic was not affected by increasing the injection time (FIG. 3B).

Altogether, these data demonstrate striking differences in the mechanisms of interaction of PD-L1 and PD-L2 with PD-1. The data obtained with PD-L1 fit with a model where a conformation change will be needed for its efficient binding with its receptor.

We finally analyzed whether this conformational change model was restricted to PD-L1:PD-1 interaction and hence due to the ligand or observed with another PD-L1 ligand like CD80. As shown in FIG. 3A, PD-L1 binding to CD80 was also associated with the conformational change model. Altogether, these data indicate that PD-L1 and PD-L2 differ in their binding to PD-1. Whereas bind to its ligands, namely PD-1 and CD80 with similar association and dissociation mechanisms.

Non Blocking PD-L1 Mabs Increase the Binding of PD-L1 to PD-1

We have also tested the ability of PD-L1 and PD-L2 mabs to prevent the interaction of PD-L1 and PD-L2 to PD-1. Anti-PD-L2 and anti-PDL1.3 mAbs prevented PD-1/PD-L2 and PD-L1 interaction respectively (data not shown and). However, anti-PDL1.1 and anti-PDL1.2 did not inhibit PD-L1/PD-1 interaction (data not shown).

As PD-L1 binding to PD-1 could induce a conformational modification of PD-L1 we reasoned that these two mAbs that do not interfere with PD-1/PD-L1 binding might affect other PD-L1 regions that might be critical for ligand-receptor interaction. Hence, we also investigated whether the anti-PD-L1 antibodies that do not block binding to PD-1 could influence this phenomenon. To do so, PD-L1 Ig proteins were incubated with a saturating concentration of PDL1.1 and PDL1.2 antibody Fabs and injected onto the PD-1 chip (FIG. 4 A). We observed that pre-incubation with both non blocking anti-PD-L1 antibodies clearly modifies the dissociation of PD-L1 Ig proteins from PD-1 chip. The PD-L1 dissociation is slower when PD-L1 is bound to either PDL1.1 or PDL1.2 Fabs. The binding of PDL1.1 or PDL1.2 Fabs to PD-L1 seems to increase the stability of the PD-L1 PD-1 interaction, may be by influencing the conformational modification of PD-L1. These data seem in line with the "conformational modification model" that we preferred to choose for the fitting of PD-L1 binding to PD-1. However, the fact that the conformational transition phenomenon was observable using the Biacore indicates that the modification of PD-L1 state is not a fast phenomenon. Taking in account these considerations we next investigated whether the conformational modification could be observed on native PD-L1 molecules expressed at the cell surface.

Figure 4B:
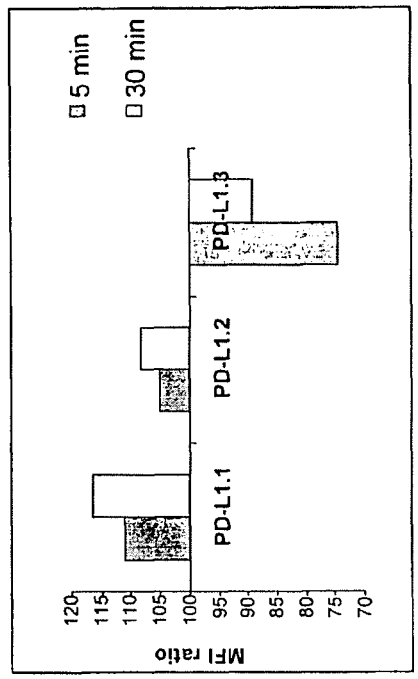
FIGS. 4A and B shows that PDL1.1 and PDL1.2 PD-L1 antibodies stabilize the binding of PD-L1 to PD-1. (A) Superimposed sensorgrams showing the injections of PD-L1 Ig recombinant proteins (grey) or the injections of PD-L1 Ig recombinant proteins pre-incubated with PD-L1 antibodies (black) onto PD-1 chip. PD-L1Ig recombinant proteins at 10 µg/ml were pre-incubated with PDL1.1, PDL1.2 or PDL1.3 PD-L1 antibody Fabs at a saturating concentration of 100 µg/ml and injected for 10 minutes at a flow rate of 10 µl/min onto the PD-1Ig chip. Sensorgrams were normalized in the Y axis and aligned in the X axis at the end of injection. (B) FACS analysis on PD-L1 expressing COS cells. PDL1.1, PDL1.2 and PDL1.3 Fab mAbs were incubated with PD-L1 expressing cells for 5 or 30 minutes. The binding of PD-1 Ig was revealed with Goat anti human (GAH) conjugated PE, the MR ratio was indicated in the Y axis. The data shown are representative of three separate experiments.
Figure 4A:
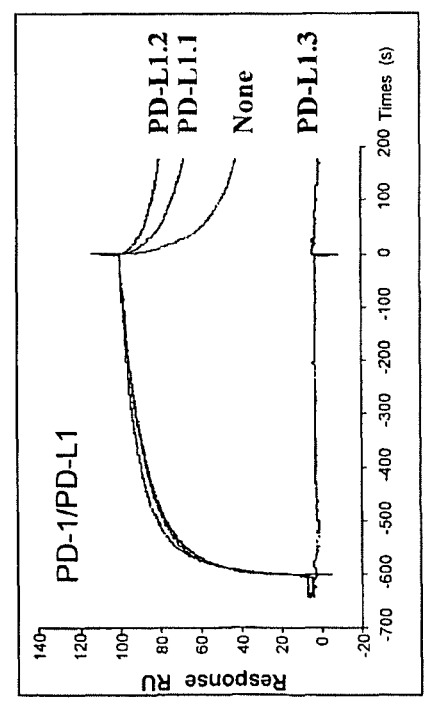

Thus, the stabilizing effect of PDL1.1 and PDL1.2 non blocking antibodies on the binding of PD-L1 to PD-1 was analysed at a cellular level. PD-L1 expressing COS cells were incubated for 5 or 30 minutes with the three different anti-PD-L1 Fabs. Then, PD-1 Ig protein binding was tested by FACS analysis. The PDL1.1 Fab pre-incubation induced an increase of the MFI due to PD-1 protein binding (FIG. 4B). This increase occurred as early as 5 minutes post-Fab injection and was further enhanced after 30 minutes. This result was in accordance with the data of the SPR analysis (FIG. 4A). As shown in FIG. 4B, both non blocking PDL1.1 and PDL1.2 induce an increase of PD-1 binding. In control, the blocking PDL1.3 Fab impaired this PD-1 binding (FIG. 4B). Same results were obtained using immature DC expressing PD-L1 (data not shown). Taken together, the non blocking PD-L1 mAbs are not neutral but in fact promote the binding of PD-L1 to PD-1.

REFERENCES

Throughout this application, various references describe the state of the art to which this invention pertains. The disclosures of these references are hereby incorporated by reference into the present disclosure.

---

The invention claimed is:

1. A PD-1 antibody obtainable from the hybridoma accessible under CNCM deposit number I-4122 or a derivative thereof having the same CDRs as the PD-1 antibody obtainable from the hybridoma accessible under CNCM deposit number I-4122.

2. A method of blocking the activity of PD-1 in a cell comprising contacting said cell with a PD-1 antibody according to claim 1, wherein said PD-1 antibody blocks the interaction of said PD-1 with PD-L1.

3. A method of blocking the activity of PD-1 in a cell comprising contacting said cell with a PD-1 antibody according to claim 1, wherein said PD-1 antibody blocks the interaction of said PD-1 with PD-L2.

4. The method of claim 2 wherein said cell is in a human or animal subject.

5. The method of claim 3 wherein said cell is in a human or animal subject.

* * * * *